United States Patent [19]
Allen et al.

[11] Patent Number: 5,340,539
[45] Date of Patent: * Aug. 23, 1994

[54] NON-INSTRUMENTED CHOLESTEROL ASSAY

[75] Inventors: Michael P. Allen, Sunnyvale; Henry J. Jeong, Palo Alto, both of Calif.

[73] Assignee: ChemTrak, Inc., Sunnyvale, Calif.

[*] Notice: The portion of the term of this patent subsequent to Nov. 25, 2007 has been disclaimed.

[21] Appl. No.: 958,519

[22] Filed: Oct. 8, 1992

Related U.S. Application Data

[63] Continuation-in-part of Ser. No. 789,059, Nov. 7, 1991, abandoned, which is a continuation of Ser. No. 474,991, Feb. 6, 1990, Pat. No. 5,132,086, which is a continuation-in-part of Ser. No. 357,045, May 24, 1989, abandoned, which is a continuation-in-part of Ser. No. 324,407, Mar. 16, 1989, Pat. No. 4,987,085, which is a continuation-in-part of Ser. No. 195,881, May 19, 1988, Pat. No. 4,999,287, and a continuation-in-part of Ser. No. 64,883, Jun. 22, 1987, Pat. No. 4,973,549.

[51] Int. Cl.$^5$ ............................................. G01N 21/00
[52] U.S. Cl. .................................... 422/56; 422/57; 422/58; 435/11; 435/28; 435/970; 436/169; 436/170
[58] Field of Search ............................ 422/56, 57, 58; 436/169, 170; 435/970, 11, 28

[56] References Cited

U.S. PATENT DOCUMENTS

| | | | |
|---|---|---|---|
| 3,907,645 | 9/1975 | Richmond | 435/11 |
| 3,925,164 | 12/1975 | Beaucamp et al. | 435/886 |
| 4,008,127 | 2/1977 | Gruber | 435/190 |
| 4,144,129 | 3/1979 | Gruber | 435/190 |
| 4,168,146 | 9/1979 | Grubb et al. | 422/56 |
| 4,186,251 | 1/1980 | Tarbutton | 435/11 |
| 4,212,938 | 7/1980 | Gruber et al. | 435/11 |
| 4,223,089 | 9/1980 | Rothe et al. | 436/165 |
| 4,366,241 | 12/1982 | Tom et al. | 422/56 |
| 4,391,904 | 7/1983 | Litman et al. | 422/56 |
| 4,426,451 | 1/1984 | Columbus | 436/165 |
| 4,435,504 | 3/1984 | Zuk et al. | 422/56 |
| 4,533,629 | 8/1985 | Litman et al. | 422/56 |
| 5,132,086 | 7/1992 | Allen et al. | 422/56 |

Primary Examiner—James C. Housel
Assistant Examiner—Laura E. Collins
Attorney, Agent, or Firm—Bertram I. Rowland

[57] ABSTRACT

An assay for determining the cholesterol level in a sample involving a bibulous strip comprising a transfer region for transporting a transport medium from a transport medium source, a sample receiving region in fluid communication with the transfer region, and a measurement region in fluid communication with the sample receiving region, and a detectable signal reagent system comprising a catalytic agent or enzyme, unbound conversion reagent and bound reagent wherein the conversion reagent reacts with cholesterol to form an intermediate product and wherein the bound reagent reacts with the intermediate product in the presence of the catalytic agent or enzyme to produce a detectable border, in which the conversion reagent is placed in the transfer region of the strip or in a region of the strip between the sample receiving and measurement regions and the signal reagent is non-diffusively bound to the strip in the measurement region, and which upon contact with the sample and the transport medium results in the production of a detectable border in the measurement region which is related to the level of cholesterol in the sample.

16 Claims, 2 Drawing Sheets

NON-INSTRUMENTED CHOLESTEROL ASSAY

CROSS REFERENCE TO RELATED APPLICATIONS

This application is a continuation-in-part of application Ser. No. 07/789,059, filed Nov. 7, 1991, now abandoned, which is a continuation of application Ser. No. 474,991, filed Feb. 6, 1990, now U.S. Pat. No. 5,132,086, which is a continuation-in-part of application Ser. No. 357,045, filed May 24, 1989, now abandoned, which application is a continuation-in-part of application Ser. No. 324,407, filed Mar. 16, 1989, now U.S. Pat. No. 4,987,085, which is a continuation-in-part of application Ser. No. 195,881, filed May 19, 1988, now U.S. Pat. No. 4,999,287 and a continuation-in-part of application Ser. No. 64,883, filed Jun. 22, 1987, now U.S. Pat. No. 4,973,549, which are incorporated herein by reference.

INTRODUCTION

1. Technical Field

The field of this invention is non-instrumented diagnostic devices and assays for determining cholesterol levels in samples.

2. Background

Cholesterol is a hydrophobic molecule found in all animals as an essential component of cell membranes and hormones and is known to be involved in other vital functions as well. Since cholesterol is present in all animal tissue, cholesterol is consumed every time food of animal origin is eaten. Although cholesterol is essential for body processes, it is not necessary for this compound to be ingested, since the liver can produce all that is needed.

Cholesterol is found and stored in blood as a fatty acid ester which is complexed with serum proteins. These cholesterol ester-protein complexes found in blood are termed lipoproteins. In this way "nature" has found a method to allow water insoluble cholesterol to become soluble in whole blood. There are two types of lipoproteins which have been identified in blood, and these two types are low density lipoproteins (LDL) and high density lipoproteins (HDL). LDL cholesterol is known to contain a high proportion of cholesterol and has been indicted as being the agent responsible for the deposition of cholesterol in artery walls. HDL cholesterol, on the other hand, is believed to transport cholesterol to the liver for removal from the blood. Thus, LDL cholesterol has been characterized as "bad" cholesterol, while HDL cholesterol has been characterized as "good" cholesterol.

A relationship has been established between total blood cholesterol (which is primarily the LDL fraction) and coronary artery disease. Guidelines have been established for adults over 20 years of age to identify risk groups associated with blood cholesterol level. These levels are as follows: <200 mg/dl is desirable blood cholesterol; 200 to 239 mg/dl is borderline high blood cholesterol; >240 mg/dl is considered high blood cholesterol.

Cholesterol levels can be controlled by both diet and cholesterol-lowering drugs. The key to such efforts to control cholesterol levels is to identify those individuals at risk. There has been an effort in the past several years to identify individuals with elevated cholesterol levels and initiate treatment. This effort is expected to lower mortality from coronary heart disease. A procedure whereby cholesterol levels could be easily and conveniently determined at home, therefore, would be particularly useful in the effort to lower mortality from coronary heart disease.

The following methodology includes assay strip design and performance characteristics for a noninstrumented whole blood cholesterol assay which is well-suited for home use. This type of home testing will improve the method for identification of those at risk and further reduce death from coronary heart disease.

Relevant Literature

Demacker et al., *Clin. Chem.* (1983) 29:1916–1922 reports the evaluation of cholesterol assay kits.

Studies associated with enzyme assays include Gochman and Schmitz, *Clin. Chem.* (1971) 17:12; Paul, *The Enzymes* (1963) 8:227–274; *Current Status of Blood Cholesterol Measurement in Clinical Laboratories in the United States; A Report from the Laboratory Standardization Panel of the National Cholesterol Education Program* (1988) 34(1):193–201, and U.S. Pat. Nos. 4,391,904, 4,366,241, 4,168,146, 4,435,504, 4,533,629, 4,504,659, and the references cited therein. See also, Zuk et al., *Clin, Chem.* (1985) 31:1144-1150.

German Patent No. 22 951 describes a filter assembly containing chemical reagents for removing cells from blood and measuring CPK.

SUMMARY OF THE INVENTION

The present invention involves methods and apparatus for use in determining cholesterol levels in samples by using a continuous flow path assay in which the cholesterol is reacted with a conversion reagent to provide an intermediate product which in turn reacts with a bound reagent on the path to produce a detectable signal having a detectable border whose distance from a predetermined site is related to the amount of cholesterol in the sample. Improved accuracy and sensitivity are obtained in the assay by placing the conversion reagent, and/or additional reagents needed to produce the detectable signal from the intermediate product and bound reagent, on the path upstream or downstream of the path region initially contacted with the sample, such that the reagents are transported by a transport medium through the bound reagent region.

DESCRIPTION OF SPECIFIC EMBODIMENTS

Figure 1:
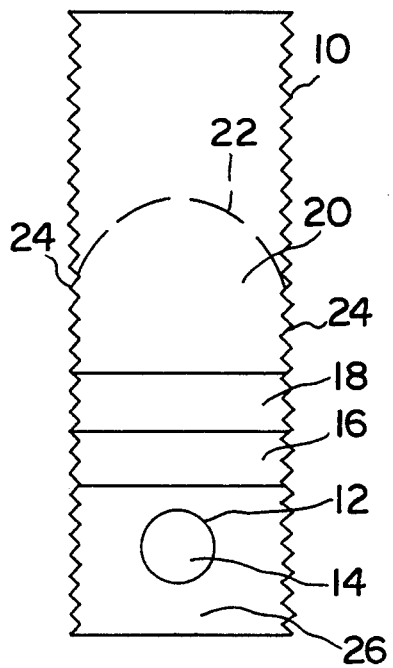
FIG. 1 is a diagrammatic plan view of a measuring strip according to this invention.

Methods and apparatus are provided for the measurement of cholesterol in a sample employing a continuous flow path, which has a transfer region, sample receiving region, an optional detectable signal reagent capturing region, and a measurement region. The presence of cholesterol and conversion reagent of the detectable signal reagent system results in production of an intermediate product, which directly or indirectly reacts with another member of the detectable signal reagent system which is bound to the surface of the measurement region. The result is the production of a detectable signal, generally a colored zone, in the measurement region. The distance of the border of the detectable signal from a predetermined site can be related to the amount of cholesterol in a sample.

Various techniques may be employed for organizing the flow path and providing for flow of a reagent solution through the sample region, the reagent capturing region, and the measurement region. In addition, various chemistries may be employed, using different types of reagent systems to produce the desired signal. The assay may be semiquantitative or quantitative. For quantitative assays, the distance of the border of the detectable signal, i.e., colored border, from a predetermined site indicates the amount of cholesterol in the sample.

The general design of such assays is set forth in co-pending U.S. patent applications Ser. No. 433,538 filed Nov. 8, 1989, which application is a continuation-in-part of Ser. No. 357,045, filed May 29, 1989, which application is a continuation-in-part of Ser. No. 324,407, filed Mar. 16, 1989, which is a continuation-in-part of Ser. No. 195,881, filed May 19, 1988, and Ser. No. 064,883, filed Jun. 22, 1987, now U.S. Pat. No. 4,973,549, which disclosures are incorporated herein by reference in their entireties.

The flow path comprises several regions, where certain regions may be overlapping, in whole or in part: (a) transfer region, (b) sample receiving region, (c) conversion reagent region (before or after the optional capture region), (d) optional capture region, and (e) measurement region. The device embodying the flow path may be of any suitable configuration, preferably a strip which has the various regions aligned in the direction of transport medium flow.

The transfer region receives the transport medium and initiates the flow of the transport medium into the flow path. For the most part, particularly with extended strips, it will be a bibulous short element which serves by capillary action to wick or transport the transport medium to the next region, normally the sample receiving region. For the most part, the transfer region will be a bibulous strip which absorbs a hydrophilic liquid and allows for transport of any reagents contained in the transport medium with or without chromatographing the components of the transport medium. Where the device is a circular disc, the transfer region will be at the center of the disc and allow for transport of the medium radially away from the center through the other regions.

The sample receiving region serves to receive the sample and to act as a bridge for transferring the transport solution to the next region. In one embodiment, prior to the time that the transfer region serves to transport the medium to the sample receiving element, adjacent regions to the sample receiving region will not be in fluid receiving relationship with the sample receiving region. In that embodiment, after receiving the sample, the sample receiving element is then permitted to be a bridging element which allows for the flow of the transport solution through the sample receiving region and into the next region.

The sample receiving region may take a number of forms but may be simply a site on the bibulous strip where the sample is placed. Alternatively, it may be a pad in fluid transferring relationship with an underlying strip with or without catalytic agents(s), such as enzyme(s), to catalytically or enzymatically convert cholesterol to produce hydrogen peroxide. Various techniques may be employed for providing a measured amount of sample to the sample receiving region. The sample may be measured by any convenient means, such as a micropipet, capillary or the like, touching the measuring device to the sample receiving region. Alternatively, an automatic mechanism may be provided as part of the device, which receives the sample on a pad having a predetermined liquid absorbing capacity, where the pad is moved from a site where the sample is received past a wiping mechanism to the site where the pad serves as a bridge between two regions in the flow path.

The conversion region strip is placed downstream from the sample receiving region. This area contains cholesterol esterase and cholesterol oxidase diffusively bound and serves to convert serum or plasma cholesterol and cholesterol ester to hydrogen peroxide.

The capture region is optional but preferred and essentially prevents a predetermined amount of cholesterol from affecting the measurement region, thereby allowing for a shorter measurement region and reduced wicking time while still expanding the distance traversed for an incremental value of cholesterol. The capture region will have a reagent which will react with the cholesterol or intermediate product which results from the reaction of the cholesterol and conversion reagent and which is present in an amount related to the amount of cholesterol present in the sample. The capture region may completely or partially overlap the sample receiving region, extend upstream from the sample receiving region, or be upstream and separate from the sample receiving region.

The capture region may employ the same reagent as the measurement region, but at a higher density. Generally, the density will be at least 20% greater, usually at least 1.5 fold greater and may be 5 fold or more greater. Usually the capture region will be less than half the area of the measurement region, usually less than about one-quarter. The capture region should be large enough to ensure substantially complete capture of the amount of reagent desired.

By providing for a capture region, which is involved with reacting with a component involved with the production of the detectable signal, between the sample receiving element and the measuring region, the dynamic range of the assay may be modified. Specifically, because a proportion of the cholesterol or intermediate product becomes bound or is reacted chemically to produce a non-interacting compound in the capture region, the amount of reagent non-diffusively bound in the measurement region may be reduced and spread over a greater area giving a lower density per unit area of the reagent in the measurement region. This results in having greater separation per unit of cholesterol, thus allowing for a more sensitive assay. It is found that greater separations can be obtained while still obtaining a clearly detectable border. Distribution of the reagent such as a leuco dye on the measurement region allows the signal generating material, such as $H_2O_2$, to move further, thereby providing additional signal height for a fixed amount of the sample. This provides higher sensitivity and precision in the assay. The capture region can be provided with a secondary reagent which reacts with the detectable signal reagent system product, so that a predetermined threshold value becomes the zero or low value observed in the measuring region.

The reaction in the capture region may involve specific binding pair member complex formation, chemical reactions involving transformation of reactants into a product, or the like. For example, one may provide for antibodies to the cholesterol, which prevent the cholesterol from reacting with the conversion reagents. Thus, one can withdraw a predetermined amount of cholesterol from the transport medium or sample prior to reaction, so that in order to have a signal in the measurement region, the amount of cholesterol must be greater than the amount that reacts with the capturing region. Alternatively, one can provide for a relatively high density of a component of the detectable signal reagent system in a relatively small area, so that there will be a strong band of signal produced in this narrow area, which may be disregarded. Rather than using a member of the detectable signal reagent system, one may use a different compound which reacts with a detectable signal reagent component which is present in a limited amount. For example, in the case of hydrogen peroxide as a detectable signal reagent component, various reactants may be present which will react with hydrogen peroxide to produce unreactive products. Illustrative reagents include metal ions or ions such as iodide.

The measuring region will usually be an extended member, which allows for the flow of the transport solution through the measuring element by means of capillary action. The measuring region will have one or more members of the detectable signal reagent system non-diffusively bound to the measuring region. The bound reagent reacts, either directly or indirectly, with the product of the cholesterol and conversion reagent to produce a detectable signal, e.g., a colored region with a discernible border. The height or distance of the observable border as a result of a detectable signal of the detectable signal reagent system, e.g., distance from the sample receiving element to the signal front, will be related to the amount of cholesterol in the sample. Reagents on the measuring region may be uniformly distributed or spread in the form of alternating equal or unequal height bands to extend the signal height for a given sample concentration. Alternatively, appearance of a signal at a predetermined area can indicate the presence or absence of cholesterol.

The detectable signal reagent system comprises a conversion reagent which reacts with the cholesterol to produce a stoichiometric amount of an intermediate product which in turn reacts, directly or indirectly, with another member of the detectable signal reagent system bound to the continuous flow path or strip to produce a detectable, e.g., colored, signal on the path or strip. The detectable signal reagent system may also comprise additional reagents, such as other intermediate components or catalysts needed to produce a detectable signal. The conversion reagent preferably includes reagents which react with cholesterol esters and cholesterol to form hydrogen peroxide. Such reagents are most preferably cholesterol esterase (EC:3.1.1.13) and cholesterol oxidase (EC:1.1.3.6). The serum cholesterol ester is hydrolyzed by the cholesterol esterase, and subsequent oxidation of the cholesterol is accomplished by the cholesterol oxidase to produce a stoichiometric amount of hydrogen peroxide. The hydrogen peroxide can in turn react with a peroxidase substrate on the continuous flow path in the presence of a catalytic agent such as horseradish peroxidase or other peroxidase to form a colored region on the path, which region relates to the level of cholesterol in the sample. The cholesterol esterase can be immobilized at 5 to 50 units/ml most preferably at 18 units/ml. The cholesterol oxidase can be immobilized at 10 to 100 units/ml, most preferably at 50 units/ml. The horseradish peroxidase can be immobilized along the flow path of the assay strip at immobilization concentrations 0.05 to 2.5 mg/ml, usually at 0.5 mg/ml. Peroxidase may also be included in the transport medium at 0.0005 to 0.050 mg/ml.

By appropriate choice of members of the detectable signal reagent system, visually observable color fronts, fluorescent signals, or the like may be obtained for a quantitative assay.

The horseradish peroxidase or other catalytic agent may be provided in the transport solution, or in one of the referenced regions of the continuous flow path during fabrication of the device, or means for providing a catalytic agent capable of facilitating the reaction between the non-diffusively bound reagent and the intermediate product may be provided. Such means for providing may be application, for example, by spraying or dipping at the time of the assay. When the catalytic agent is provided in the measurement region, the catalytic agent is preferably non-diffusively bound throughout the region.

The conversion reagent of the detectable signal reagent system is placed in the continuous flow path in the transport region, the sample receiving pad or the region between the sample receiving and measurement regions, preferably in the region between the sample receiving and measurement regions. Upon movement of the transport medium through the path, the conversion reagent is transported into contact with the sample or vice versa depending upon whether the conversion reagent is placed upstream or downstream of the sample receiving region. Any additional reagents of the detectable signal reagent system, other than the bound reagent in the measurement region, may be a part of the transport medium or placed in the continuous flow path in the transport region, in the region between the sample receiving and measurement regions, or in the measurement region, preferably in the region between the sample receiving and measurement regions. The transport medium transports these additional reagents through the path.

Other reagents may also be present in the assay. For example, detergents find particular use in the present assay to minimize or eliminate the binding of cholesterol to other proteins in the sample. Thus, detergents such as non-ionic, anionic, or cationic detergents may be employed. Of particular interest are polyoxyalkylenes, ethoxylated alkylphenols, octylphenoxypolyethoxyethanol, octylphenol-ethylene oxide condensates and polyoxyethylene lauryl ethers, or anionic detergents, such as bile acids, e.g., sodium cholate and sodium taurocholate. In addition, various sticking agents or adhesives may be employed, such as gum arabic. Also of interest will be proteins which are substantially non-interfering, which may include gelatin, casein, serum albumin, or gamma-globulins. In addition, the reagent containing regions may include preservatives, such as sucrose, polyvinyl alcohol, polyvinyl pyrrolidone, dextran, or sodium azide. Finally, a buffered solution will normally be employed for impregnating the reagent containing regions. Any convenient buffer may be employed, preferably a substantially dilute buffer, which may include phosphate, TRIS, MOPSO, borate, carbonate, or the like. Usually, the buffered solution will be at a pH in the range of about 4 to 9. The buffer concentration will generally be from about 10 to 500 mM.

The conversion medium applied to the strip typically will contain about 0.1 to 5 weight percent detergent. In the case of detergent mixtures, the weight of non-ionic detergents may be about 10 to 90 weight percent, usually about 25 to 75 weight percent, of the total detergent mixture. The binding agents or adhesives will generally be in the range of about 0.2 to 10 weight percent, more usually about 1 to 5 weight percent, of the medium. A preservative or hydrogen bonding agent may be present in about 1 to 20 weight percent, more usually about 2 to 10 weight percent. The remaining additives will generally be present in total amount of less than about 10 weight percent, more usually of less than about 5 weight percent. The remaining composition may be water, non-reactive ingredients, excipients, extenders, and the like.

The assay is carried out by impregnating a sample receiving region with the sample. In a preferred embodiment, the sample receiving region is a pad, which serves as a bridge between the other flow path elements positioned in tandem juxtaposition along their long axes. Thus the elements define one long flow path, usually comprised of differently sized bibulous strips or areas, conveniently with a separation between strips, where the sample receiving element may act as a bridge to allow for fluid flow between strips.

Blood will be the sample typically assayed for cholesterol. The sample receiving region, therefore, is preferably positioned under a red blood cell removing filtering device. The blood sample will normally be one or a series of small drops, generally having a total volume under about 100 $\mu$l, more usually about 10–50 $\mu$l. The layers through which the sample flows will usually include a mesh layer, a first membrane, and a second membrane cooperating with the first membrane to ensure the substantially complete removal of any interfering cells from the blood sample. The first cellular separation member is used to reduce the concentration of red and white blood cells received by the second filtration member. By lowering the red blood cell content about 10 to 90%, usually about 30 to 90%, of the original red blood cell content with the first membrane member, the second membrane member is able to efficiently and accurately remove at least substantially all of the red blood cells from the blood sample. Since the first membrane acts as a coarse separation means, the first membrane may take any of a wide variety of forms.

Various packings or sieving depths of filters may be employed, such as glass fibers, cellulose filters treated with red blood cell capture reagents, glass fiber filters, or synthetic fiber filters. Glass fiber filters are available from such manufacturers as Whatman, Schleicher and Schuell, MSI, and Pall. The glass fiber filters are further characterized by a glass fiber diameter in the range of about 0.5–9 $\mu$m, and a density of about 50 to 150 g/m$^2$. The glass fiber filters may be illustrated by S&S Glass 30, Whatman GFD, and S&S 3362.

Other coarse separation membranes may include cellulosic membranes, e.g., filter paper, to which red blood cell binding proteins or agglutination agents are immobilized. Such proteins may include lectins, antibodies specific for RBC surface membrane proteins, thrombin, ion exchange agents, etc. The preparation of such filters by conjugating proteins or other agents to cellulose is well known. Cellulose may be activated in a wide variety of ways employing carbodiimide, carbonyl diimidazole, cyanogen bromide, chloroacetic acid, where the acid may then be activated with carbodiimide, or the like. The literature is replete with examples of binding of proteins to cellulosic membranes for a variety of reasons, which techniques may be employed here. Alternatively, multiple layers of coarse separation membranes may be employed.

When two membranes are used, the second membrane will preferably be immediately beneath the first membrane and will be in fluid receiving relationship with the first membrane, either in contact with the first membrane or in close proximity thereto. Generally, the spacing between the first and second membranes will not exceed a distance which inhibits fluid flow, so that fluid readily flows from the first to the second membrane. The non-asymmetric membranes which are employed will be those in the medium porosity range, having an average porosity in the range of about 0.65 $\mu$m to 7 $\mu$m, preferably about 1 to 5 $\mu$m, where the pores may or may not be of substantially uniform diameter through the membrane. By contrast, where an asymmetric membrane (i.e., one wherein the diameter of the pores vary from one surface to the other) is employed, desirably the membrane will have a minimum porosity not less than about 0.2 $\mu$m, preferably not less than about 0.45 $\mu$m, and the maximum porosity will generally not exceed about 40 $\mu$m, more usually not exceeding about 20 $\mu$m. Illustrative microporous membranes which may find use include Filterite polysulfone asymmetric, 20 $\mu$m–0.45 $\mu$m; Sartorious cellulose acetate, 1.2 $\mu$m; and Nucleopore 1.0 $\mu$m.

The choice of the second membrane is important, since the amount of red blood cell lysis is dependent on a number of factors. Depending on the size of the pores, the amount of lysis will greatly vary. Since lysis results in release of colored cell components, which interfere with detection of the border in the measuring strip and may act to decompose detectable signal reagent system components, particularly hydrogen peroxide, merely removing cells is insufficient. A further consideration is the pressure differential across the membranes. Again, the appropriate choice of membranes will affect the pressure drop and forces acting on the cells, which in turn can affect the stability of the cells.

Thus, the two membranes serve to act together to efficiently and accurately remove red blood cells from the blood sample with little, if any, hemolysis, so as to provide a plasma or serum sample which may be accurately analyzed without interference from hemolytic products, such as heme.

The sample receiving region will be immediately beneath the red blood cell removing membranes and in fluid receiving relationship with the membranes. The sample receiving region will normally be a bibulous member able to absorb the fluid. Various bibulous materials may be used, such as cellulosic materials e.g., paper, or the like. The sample receiving region will usually be of a size in the range of 5 to 100 mm$^2$ surface area, usually not more than 50 mm$^2$ surface area, and a thickness in the range of about 0.1 to 2 mm, having a volume capacity of from about 1 to 75 $\mu$l. When the sample receiving region is a pad, the pad may be round, square, rectangular, quadrilateral, or polygonal, depending on the manner in which it is to be used to act as a bridge for the other members of the flow path. For further characterization, see copending U.S. patent application Ser. No. 195,881, filed May 19, 1988, now U.S. Pat. No. 4,999,287.

The applied sample will be absorbed in the sample receiving region and may extend outside the region, both upstream and downstream, depending upon the size of the region, the nature of the assay, and the nature of the upstream and downstream regions. In one embodiment, the sample is prevented from interacting with the adjacent bibulous members when sample is transferred to the sample receiving region.

Various techniques may be employed to prevent transfer of the sample from the sample receiving region (e.g., a pad) to the other regions prior to flow of the transport medium. Of particular interest is the use of a slide which can be moved from a first position, where the sample receiving region receives the sample, to a second position where the sample receiving region serves as a bridge between the two other regions of the flow path. The slide therefore prevents sample from spreading to the other regions of the flow path, before it is time to carry out the assay. The path of the sample receiving region, in moving from the site at which the sample is received to the site where it is in the flow path, may provide for means for removing excess sample from the sample receiving region. Such means provides for a quantitative measure of the amount of sample received by the sample receiving region. Thus, by having a region in the path of the slide which is narrowed, so as to remove unabsorbed sample medium, without significantly squeezing the sample receiving region, the amount of sample absorbed by the sample receiving region can be relatively accurately reproduced. The narrowing may be as a result of a convexity, such as a rod in relief, a roller, or any convenient scraping means. The narrowing of the path should provide a space about equal to or slightly less than the wet thickness of the sample receiving region. The slide, therefore, not only serves to move the sample receiving region, but also to meter the amount of fluid absorbed by the sample receiving region.

Besides the slide mechanism, other flow inhibition means may be employed, usually comprising an inert non-porous film, which blocks transfer from the sample receiving element to the bibulous members of the flow path. The amount of sample accepted by the sample receiving element and involved in the assay medium may be controlled by providing for transfer of fluid beyond the amount saturating the sample receiving element through a non-wetting screen into an absorbent layer. After addition of the sample to the sample receiving element, and an incubation of up to about 30 minutes, the porous non-wetting material and absorbent layer are removed, leaving the sample receiving element as the sole repository of sample for the assay. Where a wiping film is employed it will be removed upon saturation of the sample receiving element. (See U.S. patent application Ser. No. 324,407, filed Mar. 16, 1989.)

The entire flow path may have a length of about 25 to 200 mm, more usually from about 50 to 150 mm, preferably about 100 mm. About 25 to 90% of the length of the flow path will be the measurement region comprising the quantitation zone, optionally a conversion region and mixing region and/or a threshold value region. The conversion region and mixing and/or threshold value regions will generally be about 5 to 50% of the flow path. The strips which provide for flow of fluid to and from the sample receiving element may be of the same or different length and each will generally be from about 5 to 25 mm, more usually about 10 to 20%, of the length of the flow path. The upstream strips may be part of the measurement region strip, or independent entities. Alternatively, this strip may be used to control the threshold value. The sample receiving region will generally be from about 1 to 10%, more usually from about 2 to 8% of the length of the flow path; the longer the flow path, the larger the sample receiving region may normally be. The width of the strips may be varied, usually being at least about 2 mm and not more than about 10 mm, preferably about 3 to 7 mm.

Any convenient material may be used for the various bibulous parts of the assay strips forming the flow path. Usually, the thickness of the bibulous components will be in the range of about 0.05 to 2.0 mm, more usually 0.15 to 0.75 mm. A wide variety of bibulous supports may be employed, particularly cellulosic supports, such as chromatography paper, silica on a support, alumina on a support, and polymeric membranes such as nitrocellulose and nylon. The characteristics of the bibulous material employed for the measurement region include the need in many instances to covalently or irreversibly bind an indicator molecule to the support, to develop a clear and sharp color, and to ensure that the fluid is capable of flowing at a convenient rate through the bibulous members.

Of particular interest is an assay device which is self-contained and only requires the sample for carrying out the assay. The device may serve as a one-step diagnostic test device using a disposable cassette format. The device may be fabricated of three individual injection molded parts into which various components of the assay system are associated. These include the filtration medium designed to separate plasma from whole blood, means for metering a precise sample volume, a glide to transfer the sample receiving element to the transfer and measurement elements and to release a transport and reagent solution. The transport solution initiates capillary migration through the flow path resulting in the development of a detectable boundary related to the amount of analyte in the sample.

Where a reduced amount of the product resulting from reaction of the cholesterol with an enzyme is present in the measuring region due to capture of such product in the capture region, it will frequently be desirable to have a lower concentration of members of the detectable signal reagent system than would be used in the absence of the capturing region. For example, where hydrogen peroxide is the product in a cholesterol assay, the optimum amount of non-diffusively bound measurement reagent such as a substrate for horseradish peroxidase is in the range of about 0.25 to 0.50 mg/ml in the dip immobilization solution, while in the present embodiment using a capturing region the dip concentration of peroxidase substrate may be lowered by 10 to 75% to a range of 0.05 mg/ml to 0.45 mg/ml.

The subject invention is now considered in light of the drawings which depict several preferred embodiments of the present invention. In a preferred embodiment in FIG. 1, a strip 10 is provided which has a scored area 12 which includes pad 14 as the sample receiving element for receiving the sample. Pad 14 may be removed from the scored area 12 and dipped in the sample to provide for a semiquantitative measurement of the amount of sample absorbed by the sample receiving element 14. After dipping the sample receiving element into the sample, it is then returned to the scored area 12 and firmly fitted into the scored area so as to be part of device 10. The region below, i.e., upstream, from the sample receiving region is the transport region 26 which is used to wick up the transport medium.

Downstream from the sample receiving element 14 is conversion reagent region 16. In this region, for example, one would have cholesterol esterase and cholesterol oxidase for reacting with the cholesterol to produce hydrogen peroxide.

Downstream from the conversion reagent region is the capture region, a narrow zone which serves to capture a predetermined amount of a component of the detectable signal reagent system which is present in limited amount as a result of being present in an amount related to the amount of cholesterol in the sample. In this situation, again using hydrogen peroxide production as illustrative, one could use a leuco dye which reacts with hydrogen peroxide in the presence of peroxidase. Thus, in region 18, one would produce a deep color if cholesterol is present in excess of a threshold value determined by the amount of dye in region 18. This dye could be spotted and dried at the base of region 20 thus eliminating the need for a discrete region and producing a similar step-gradient of reactive dye along the flow path of the assay strip. Region 20 would have a much lower density of dye throughout the region so as to allow for production of a border, where one can detect the end of the reaction between the hydrogen peroxide and the dye. Desirably a rocket as depicted by broken line 22 is obtained, where one can clearly delineate the top of the rocket from the region immediately upstream from line 22. Desirably, the side edges 24 are perforated, since this appears to provide for a sharper delineation of the border. See U.S. Pat. No. 4,757,004.

Figure 2:
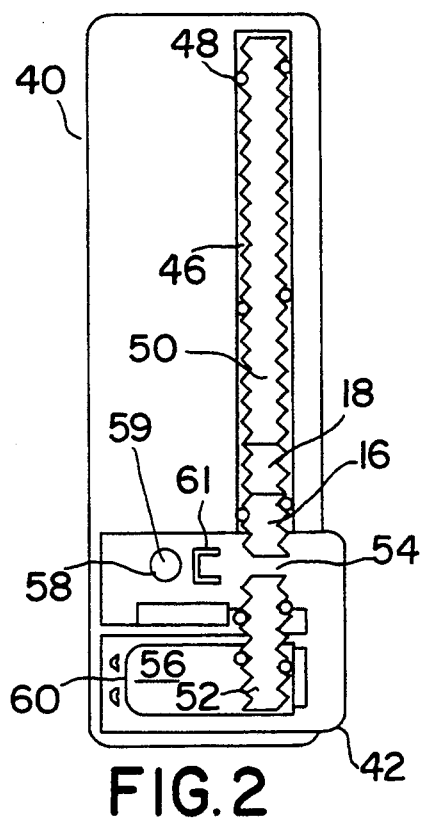
FIG. 2 is a diagrammatic plan view of the base plate and slide of an alternate embodiment according to this invention.
Figure 3A:
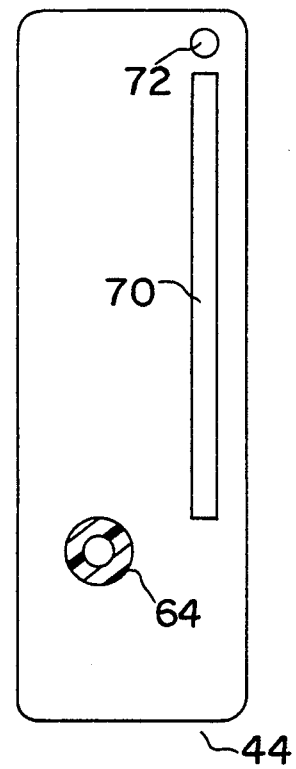
FIGS. 3a and 3b are diagrammatic plan views of an intermediate plate which covers the base plate, and of the plate inverted to show the underside, respectively.
Figure 3B:
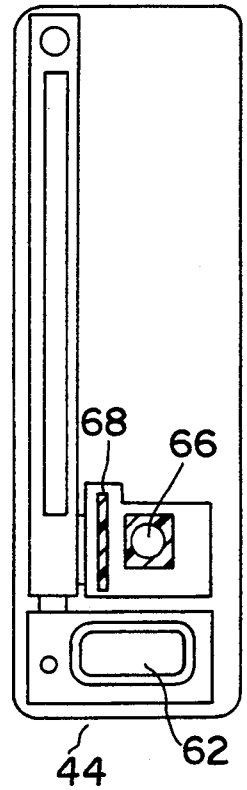
Figure 4:
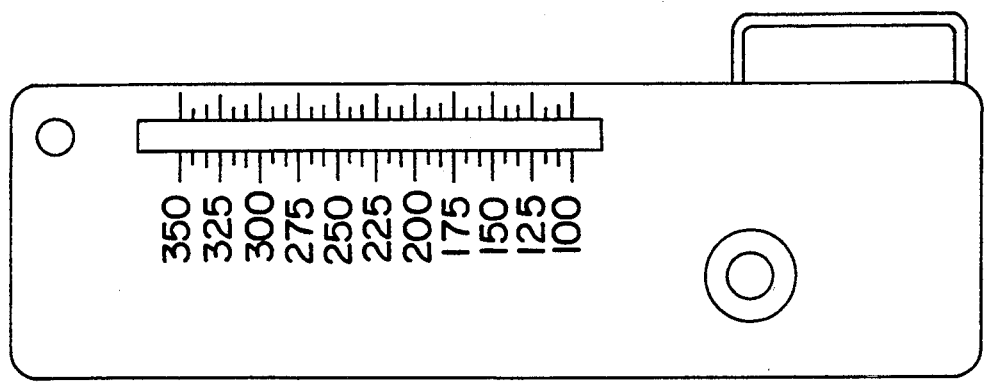
FIG. 4 is a planar view of an assembled device.

A more sophisticated device is shown in FIGS. 2 to 4. The invention may be fabricated from three injection molded parts or by any other convenient process. The parts comprise a base plate 40, a slide 42 and a cover plate 44, as shown in FIG. 2 and 3. The base plate 40 consists of a cutout to accept the slide 42, a slot 46 with locating pins 48 into which the quantitation strip 50, conversion reagent strip 16, capture region strip 18, and bibulous strip 52 are precisely positioned, maintaining about a 3 mm gap 54 between them, and a well 56 designed to capture the released transport solution, e.g., wicking buffer.

The slide 42 consists of a vented receptor site 58 into which the sample receiving pad 59 is inserted, an arm 60 with shearing action designed to facilitate the release of the transport solution from a pouch or a foil sealed container which is housed in well 62 of cover plate 44, and a snap 61 to lock the slide in place, once pulled. The sample receiving pad may have antibodies which react with the cholesterol to prevent the cholesterol from reacting with detectable signal reagent system components. Thus, for example, a predetermined amount of cholesterol can be inhibited from reacting with enzyme to produce hydrogen peroxide.

The cover plate 44 consists of a well 62, which houses a sealed foil pouch (not shown) containing the transport solution or the well 62 may be filled with transport solution and covered with a peelable foil seal. The cover plate has an orifice 64 for the introduction of the sample. Underneath orifice 64 are filters 66, for separating cells from blood samples. The filtration system may comprise dual glass fiber disks and a final filtration membrane in order to deliver cell free plasma to the sample receiving element. The cover plate also comprises the squeegee metering bar 68, which serves to control the volume of sample absorbed by the sample receiving element, as well as a viewing slot 70. At the top of the viewing slot 70 is an indicator hole 72, which changes color when the test is complete to inform the user that a reading may be taken.

The final assembly is depicted in FIG. 4, where the assembled device is obtained by introducing the slide 42 into base plate 40, positioning transfer strip 52, conversion reagent strip 16, capture region strip 18, and measurement strip 50 at their appropriate sites, introducing the transport solution pouch into well 62 or as indicated above, filling well 62 with transport solution and sealing with a Poly-foil seal, assembling the cover plate and base plate and then sealing, conveniently by sonic welding, the base plate and the cover plate. This procedure locates the sample receiving site of the slide directly beneath the filtration media of the cover plate, as well as locating the shearing points of the slide beneath the foiled sealed pouch located in the cover plate.

In order to carry out a cholesterol measurement, the user lances a finger and applies a hanging drop of blood to the application site, which is a white central well with a red or black border. When the white center is no longer visible, a sufficient amount of blood has been applied. A fill to line may also be included which is located about 0.5 to 1 mm above the filters around the bottom of the sample well. When the sample covers the line, a sufficient amount of blood has been applied. The user then waits about 30 seconds to 2 minutes or more to allow adequate filtration and recovery of plasma onto the sample receiving pad.

The slide is then pulled until it snaps into place. At this point the sample receiving pad containing the plasma sample has been metered by the squeegee metering bar and is brought into contact and fluid transferring relationship with the transfer region and the measurement region or the reagent region bridging under the two mm gap. The shearing points of the slide have also pierced the foil seal of the pouch in the well of the cover plate, releasing the transport solution into the receiving well in the base plate. The transport solution is 0.10 to 2 ml of an aqueous buffer which may contain a catalytic agent such as horseradish peroxidase in sufficient amount to insure rapid reaction of the hydrogen peroxide and dye or the horseradish peroxidase may be present diffusibly bound on the strip either upstream or downstream of the sample receiving region, or non-diffusively bound in the measurement region. Upon contact of the strip with the transport solution, the strip assembly begins wicking up the transport solution which washes the cholesterol esterase and cholesterol oxidase enzymes into the sample, or vice versa depending upon the relative placement of enzymes and sample, and further washes the hydrogen peroxide reaction product of the enzymes and cholesterol, as well as the horseradish peroxidase when present upstream from the measurement region, into the measurement region of the strip. When the catalytic agent such as horseradish peroxidase is present non-diffusively bound in the measurement region, these same components including the hydrogen peroxide reaction product of the enzymes and cholesterol are transported to the horseradish peroxidase in the measurement region.

The measurement region is impregnated with a peroxidase substrate, particularly a modified N,N-dimethylaniline. (See U.S. patent application Ser. No.

195,881, filed May 19, 1988, now U.S. Pat. No. 4,999,287.) The reaction of the reagents results in a colored region with a defined boundary, thereby giving the user a precise reading of the cholesterol level above a threshold level. This reading is made when the color indicator site above the viewing slot shows the test is complete. Normally, it will take fewer than about 15 minutes for the assay to be complete, reading the peak of a colored area in the viewing slot.

The following examples are offered by way of illustration and not by way of limitation.

EXPERIMENTAL

EXAMPLE 1

This example illustrates the separation between cholesterol levels that can be obtained through placement of the cholesterol conversion reagent on the strip in the transfer region, in the region between the sample receiving and measurement regions on the sample receiving or in the transport solution.

Figure 6:
FIGS. 5 and 6 are diagrammatic plan views of various embodiments of a laminated measuring strip according to the invention.
Figure 5:
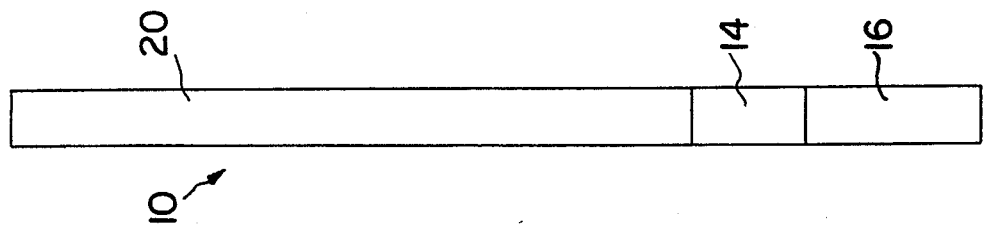

In carrying out the assay for cholesterol, a device strip 10 was prepared having an overall length of about 95 mm; 12 mm of which was the transfer region 26, about 7 mm was for the sample receiving pad 14, and the remainder was the measurement region 20, as seen in FIG. 5. The strip was made of Whatman 31ET paper where a modified N,N-dimethylaniline was covalently linked to the paper with MBTH being immobilized passively in the measurement region. This strip configuration was used when the cholesterol conversion reagents are on the sample receiving pad, the transfer region or in the transport solution. When the conversion reagents are positioned between the sample receiving and measurement regions, an additional strip area is included directly upstream from the sample receiving area. This strip area is 5–15 mm long, preferably 10 mm long, as seen in FIG. 6 and is called the conversion pad 16.

The conversion solution comprised 5.33 g sodium phosphate dibasic, 1.25 g sucrose, 1 ml Nonidet P-40, 1.0 g cholic acid, 0.83 g Mega-8, 0.71 g sodium potassium tartrate, 0.65 g sodium nitroprusside, 0.577 g sodium stannate, and 0.01 g sodium azide, after the addition of which the solution was adjusted to pH 7.0, and 1800 units of cholesterol esterase and 5000 units of cholesterol oxidase added thereto, and the volume brought to 100 ml. The strip was wetted with this solution in the conversion region and dried. Each test contains about 0.18 units cholesterol esterase and 0.60 units of cholesterol oxidase.

The wicking buffer or transport solution was comprised of 0.05M sodium phosphate, 2 mg/ml BGG, 0.005 mg/ml HRP, 0.01% gentamycin, and 0.01% Nonidet P-40.

The resulting device was tested using three calibrators at different levels provided by the College of American Pathologists (CAP), with cholesterol levels at 137, 234 and 333 mg/dl which use lyophilized human serum. Calibrators were reconstituted fresh each day.

Four modifications of the above device were tested for separation (in mm) between the tri-level CAP calibrators. The device modifications involved the location of the conversion reagents: (A) sample receiving region, (B) transport solution, (C) transfer region, and (D) region between the sample receiving and measurement regions.

In carrying out the assay using the above four device configurations, a 10 μl serum sample was placed on the sample receiving pad, and the transport solution allowed to wick up the strip. The cholesterol reacts with the conversion reagents, specifically the cholesterol esterase and cholesterol oxidase to form hydrogen peroxide, which in turn reacts with the MBTH in the presence of the horseradish peroxidase solution to produce a blue color. After the wicking was complete, the color front height was measured, which color front height is directly correlatable with the serum cholesterol level.

With the above modified designs, separation improved to provide from 6.6 to 8.7 mm between each 100 mg/dl change. This compared with a 6.7 to 7.2 mm separation between every 100 mg/dl change using the configuration in which the conversion reagents were placed in the sample receiving region. Overall, there was an observed increase in separation over the full assay range of about 200 mg/dl with the configurations in which the conversion reagent was placed in the transfer region, or in the region between the sample receiving and measurement regions, as compared to the configuration in which the conversion reagent was placed in the sample receiving region. The results are summarized in Table 1A.

To further demonstrate the placement of the cholesterol conversion reagents in the transport solution a device was constructed using the cassette system shown in FIGS. 2 through 4. This embodiment includes a measurement region 50 which extends to the sample receiving pad, a sample receiving pad 58, and a transfer region 52. The cholesterol esterase and cholesterol oxidase were included in the transport solution.

The assembled cassettes were run according to the following assay protocol.

Assay Protocol:
1. Apply 40 uL of serum calibrator to the cassette.
2. Wait 2 minutes and pull the slide.
3. Add 0.65 ml of wicking reagent containing HRP, CE and CO.
4. Allow wicking to run to completion and then record the migration height.

The results shown in Table 1B demonstrate good assay performance with an overall separation of 22 mm.

TABLE 1A

| Location of Conversion Reagents | Separation Cholesterol (mg/dl)[1] | | | Signal (mm) | | |
|---|---|---|---|---|---|---|
| | 137–173 | 234 | 333 | 137–234 | 234–333 | 137–333 |
| A. Sample Receiving Region | 27.3 | 34.0 | 41.2 | 6.7 | 7.2 | 13.9 |
| B. Transport Solution | 34.5 | 42.0 | 46.5 | 7.5 | 7.5 | 12.0 |
| C. Transfer Region | 26.0 | 34.7 | 41.3 | 8.7 | 6.6 | 15.3 |
| D. Region Between Sample Receiving and Measurement Regions | 26.0 | 33.7 | 41.3 | 8.7 | 7.6 | 15.3 |

[1]College of American Pathologists serum Calibrator set.

TABLE 1B

| Location of Coversion Reagents | Cholesterol (mg/dl) | | | Signal Separation (mm) | | |
|---|---|---|---|---|---|---|
| | 148 | 230 | 328 | 148-230 | 230-328 | 148-328 |
| Transport Solution | 15.5 | 27.7 | 37.5 | 12.2 | 9.8 | 22.0 |

EXAMPLE 2

This example illustrates the separation between cholesterol levels that can be obtained through placement of an additional reagent of the detectable signal reagent system, the horseradish peroxidase which participates in the reaction of the hydrogen peroxide intermediate product with the peroxidase substrate to produce a detectable signal, on the strip in the transfer region or in the region between the sample receiving and measurement regions, as compared to in the transport solution. This example illustrates that the results vary depending on the location of the peroxidase enzyme.

In carrying out the assay for cholesterol, the same device and general protocol was used as in Example 1 and illustrated in FIG. 6. The cholesterol conversion reagents were placed on the strip in the conversion reagent region.

Three modifications of the device were tested for separation (in mm) between the tri-level CAP calibrators. The design modifications involved the location of the horseradish peroxidase: (A) transport solution (control), (B) transfer region, and (C) region between the sample receiving and measurement regions.

With the above modified design, curve separation between the 137 and 333 mg/dl CAP calibrators was 12.0 mm when the peroxidase is in the transport solution; 23.3 mm when the peroxidase is in the transfer region. This compared with a 4.4 to 7.5 mm, separation between every 100 mg/dl change using the configuration in which the horseradish peroxidase was placed in the transport solution. Overall, there was observed 95.8% and 41.2% increases in separation, respectively, over the full assay range of about 200 mg/dl with the configuration in which the horseradish peroxidase was placed in the transfer region or in the region between the sample receiving and measurement regions, as compared to the configuration in which the horseradish peroxidase was placed in the transport solution. The results are summarized in Table 2.

TABLE 2

| Location of Horseradish Peroxidase | Cholesterol (mg/dl)[1] | | | Signal Separation (mm) | | |
|---|---|---|---|---|---|---|
| | 137 | 234 | 333 | 137-234 | 234-333 | 137-333 |
| A. Transport Solution (Control) | 34.5 | 42.0 | 46.5 | 7.5 | 4.4 | 12.0 |
| B. Transfer Region | 32.7 | 47.0 | 56.0 | 14.3 | 9.0 | 23.3 |
| C. Region Between Sample Receiving and Measurement Regions | 32.2 | 40.0 | 49.0 | 7.8 | 7.0 | 16.8 |

[1]College of American Pathologists serum Calibrator set.

EXAMPLE 3

This example illustrates effect of placement of the horseradish peroxidase (HRP) on the measurement region, as compared to in the transport solution. It also illustrates the effect of horseradish peroxidase concentration on the migration height for a mid-level (234 mg/dl) CAP calibrator. This example shows that the height varries depending on the location of the horseradish peroxidase enzyme and its concentration.

In carrying out the assay for cholesterol, the same device and general protocol was used as in Example 1 and Example 2 and illustrated in FIG. 6. The cholesterol conversion reagents were placed on the strip in the conversion reagent region 16. Horseradish peroxidase was coated on the measurement region along with the horseradish peroxidase substrates MBTH/DMA.

Two modifications of the device were tested for migration height using the mid-level (234 mg/dl) CAP calibrator. The design modifications involved the location of the horseradish peroxidase: (A) transport solution (control), and (B) measurement region.

One of the two design modifications was evaluated by adding horseradish peroxidase to the MBTH dip solution at seven concentrations ranging from 0.0025 mg/ml to 1.0 mg/ml. Paper which had DMA non-diffusively bound were dipped in each of the seven solutions and then dried. For the other design modification the HRP was added into the transport solution at the different concentrations. A mid-level (234 mg/dl) CAP calibrator was run and migration height (in mm) was measured and recorded for each design modification as indicated in Table 3.

The performance of the assay strip, as indicated by the migration height, with horseradish peroxidase coated in the measurement region can be compared to the performance of the assay strip when horseradish peroxidase is present in the transport solution.

Both assay strip designs show similar dose response with respect to horseradish peroxidase concentration such that lower horseradish peroxidase concentration increases the migration height. Furthermore, both assay strip designs provide dark color bands with minimal background and sharp color fronts except for the highest horseradish peroxidase concentration (1.0 mg/ml), where the color fronts were fuzzy and somewhat difficult to read.

For the mid-level CAP calibrator, the increase in migration height for the assay strip having horseradish peroxidase coated on the measurement region varied from about 28% to about 50%, depending on concentration, as compared to the assay strip having horseradish peroxidase in the transport solution.

TABLE 3

| HRP Concentration (mg/ml) | HRP located in Transport Solution Migration Height (mm) | HRP coated on Measurement Region Migration Height (mm) |
|---|---|---|
| 0.0025 | 42.5 | 57.5 |
| 0.005 | 40.0 | 55.0 |
| 0.025 | 34.0 | 51.0 |
| 0.087 | 32.0 | 41.0 |
| 0.17 | 29.0 | 40.0 |
| 0.4 | 26.5 | 34.5 |
| 1.0 | * | * |

*Color fronts appeared fuzzy.

It is evident from the above results that a number of substantial advantages accrue with proper placement of the cholesterol conversion reagent and horseradish peroxidase. By providing for placement of the cholesterol conversion reagent and/or horseradish peroxidase on the strip in the transfer region, in the region between the sample receiving and measurement regions, or in the measurement region, the distance traversed for an incremental value of cholesterol is varried. Also, the concentration of horseradish peroxidase may be chosen to increase the migration distance. Thus, higher sensitivity is achieved, while beneficial performance characteristics are obtained.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A device for determining the cholesterol or cholesterol ester level in a sample, said device comprising:
   (a) a first bibulous strip comprising a transfer region for transporting a transport medium from a transport medium source,
   (b) a bibulous member comprising a sample receiving region;
   (c) a second bibulous strip comprising a conversion reagent region,
   (d) a third bibulous strip comprising a measurement region;
   wherein said sample receiving region is in fluid communication with said transfer, conversion, and measurement regions, or can be moved into fluid transfer relationship with said transfer, conversion, and measurement regions; such that when said sample receiving region is moved into fluid transfer relationship with said transfer, conversion, and measurement regions, said device further comprises;
   (e) means for moving said sample receiving region from a first site for receiving said sample to fluid transfer relationship with said transfer, conversion, and measurement regions;
   (f) conversion reagent capable of reacting with cholesterol and cholesterol ester to form an intermediate product, said conversion reagent present on said second strip upstream from said measurement region, any additional conversion reagent being present on the sample receiving region, on the transfer region, or in said transport medium, such that movement of the transport medium through said second strip will bring the conversion reagent and cholesterol together to react to form said intermediate product; and
   (g) non-diffusively bound reagent in the measurement region which reacts in the presence of said intermediate product to produce a detectable border related to the cholesterol or cholesterol ester level in said sample.

2. The device of claim 1, further comprising means for providing a catalytic agent capable of causing a reaction with said intermediate product to result in a reaction with said non-diffusively bound reagent, such that when said means for providing a catalytic agent provides said catalytic agent in said measurement region said catalytic agent is non-diffusively bound throughout said measurement region.

3. The device of claim 1, further comprising horseradish peroxidase in the transport medium, on the transfer region or on the region between the sample receiving and measurement region.

4. The device of claim 2, wherein said conversion reagent comprises cholesterol esterase and cholesterol oxidase and said intermediate product is hydrogen peroxide.

5. The device of claim 4, wherein said catalytic agent is horseradish peroxidase.

6. The device of claim 2, wherein said device further comprises a capture region on said sample region or upstream from said measurement region, which capture region diminishes a predetermined portion of reaction of said bound reagent in said measurement region.

7. The device of claim 2, wherein said non-diffusively bound reagent is a leuco dye.

8. The device of claim 2, wherein said device comprises a transport solution container.

9. The device of claim 8, wherein said transport solution comprises at least one or more of cholesterol esterase, cholesterol oxidase or peroxidase.

10. A device for determining the cholesterol or cholesterol ester level in a sample, said device comprising:
    (a) a first bibulous strip comprising a transfer region for transporting a transport medium from a transport medium source;
    (b) a bibulous member comprising a sample receiving region;
    (c) a second bibulous strip comprising a conversion region;
    (d) a third bibulous strip comprising a measurement region;
    wherein said sample receiving region is in fluid communication with said transfer, conversion, and measurement regions, or can be moved into fluid transfer relationship with said transfer, conversion, and measurement regions; such that when said sample receiving region is moved into fluid transfer relationship with said transfer, conversion, and measurement regions, said device further comprises;
    (e) means for moving said sample receiving region from a first site for receiving said sample to fluid transfer relationship with said transfer, conversion, and measurement regions;
    (f) conversion reagent comprising cholesterol esterase and cholesterol oxidase capable of reacting with cholesterol and cholesterol ester to form hydrogen peroxide, said conversion reagent being present on said second strip, said second strip being present in a region between the sample receiving and measurement regions such that movement of the transport medium through said second strip will bring the conversion reagent and cholesterol together to react to form an intermediate product;
    (g) non-diffusively bound reagent in the measurement region which reacts in the presence of said intermediate product to produce a detectable border related to the cholesterol or cholesterol ester level in said sample; and
    (h) means for providing a peroxidase agent capable of causing a reaction with said hydrogen peroxide, such that when said means for providing a peroxidase provides said peroxidase in said measurement region said peroxidase is non-diffusively bound throughout said measurement region.

11. The device of claim 10, wherein said intermediate product is hydrogen peroxide.

12. The device of claim 11, wherein said peroxidase is horseradish peroxidase.

13. The device of claim 10, wherein said device further comprises a capture region on said sample region or upstream from said measurement region, which capture region diminishes a predetermined portion of reaction of said bound reagent in said measurement region.

14. The device of claim 13, wherein said capture region is downstream from said sample receiving region and comprises a reactant capable of reacting with hydrogen peroxide.

15. The device of claim 10, wherein said non-diffusively bound reagent is a leuco dye.

16. The device of claim 10, wherein said sample receiving region is out of fluid transfer relationship with said transfer and measurement regions and further comprising means for moving said sample receiving region from a first site for receiving said sample to fluid transfer relationship with said transport and measurement regions.

* * * * *